US010105389B1

(12) United States Patent
Alliger

(10) Patent No.: US 10,105,389 B1
(45) Date of Patent: Oct. 23, 2018

(54) METHOD AND COMPOSITIONS FOR TREATING CANCEROUS TUMORS

(71) Applicant: Howard Alliger, Melville, NY (US)

(72) Inventor: Howard Alliger, Melville, NY (US)

( * ) Notice: Subject to any disclaimer, the term of this patent is extended or adjusted under 35 U.S.C. 154(b) by 0 days.

(21) Appl. No.: 15/475,704

(22) Filed: Mar. 31, 2017

Related U.S. Application Data

(60) Provisional application No. 62/337,073, filed on May 16, 2016, provisional application No. 62/317,330, filed on Apr. 1, 2016.

(51) Int. Cl.
| | | |
|---|---|---|
| *A61K 33/00* | (2006.01) | |
| *A61K 47/18* | (2017.01) | |
| *A61K 47/10* | (2017.01) | |
| *A61K 45/06* | (2006.01) | |

(52) U.S. Cl.
CPC .............. *A61K 33/00* (2013.01); *A61K 45/06* (2013.01); *A61K 47/10* (2013.01); *A61K 47/18* (2013.01)

(58) Field of Classification Search
CPC ...................................................... A61K 33/00
See application file for complete search history.

(56) References Cited

U.S. PATENT DOCUMENTS

| | | | | |
|---|---|---|---|---|
| 2002/0098246 A1* | 7/2002 | Howes | .................... | A61K 33/00 424/613 |
| 2011/0262525 A1* | 10/2011 | Wang | ..................... | A61K 31/00 424/450 |

OTHER PUBLICATIONS

Agus DB, et al. Stromal Cell Oxidation: A Mechanism by Which Tumors Obtain Vitamin C1. Cancer Research, 1999;59:4555-4558.
9 Weaknesses to focus on when fighting cancer and h ow to use them to your advantage.AIM—Arizona Integrative Medical Center Apr. 16, 2016. www.drstallone.com/cancer_article4.htm.
Alliger H, et al. Healing and Disinfectant Properties of the DioxiCare System. A Comparative Evaluation of Six Formulations. Frontier Pharmaceutical, Inc, 2001. Melville NY.
AIDS Treatment with CIDERM Anti Viral Compound. ARCO Research, Inc. 1996.
Atiyah TS. The Value of Local Application of Hydrogen Peroxide Solution at the Site of Wound after Mastectomy for Breast Carcinoma in Reducing Local Recurrence of the Tumor. Iraqi J Med Sci, 2010;8(3):3-13.

(Continued)

*Primary Examiner* — Benjamin J Packard
(74) *Attorney, Agent, or Firm* — Henry D. Coleman; R. Neil Sudol

(57) ABSTRACT

The present invention relates to the use of chlorine dioxide compositions for treating cancerous tumors. The present invention relates to compositions and methods for treating cancerous tumors, including naïve, metastatic and recurrent cancers. The compositions comprise chlorine dioxide in an effective amount, which is injected into the cancerous tumor at least once, and often at least several times over the course of treatment. The chlorine dioxide compositions are injected directly into the cancerous tumor and the resulting tumor is effectively eliminated from the patient or subject over a period of one to several days to a few weeks, often after a single injection, or multiple injections at one session into the tumor. Often, an initial injection or multiple injections at one session are sufficient to dissolve the cancerous tumor. Often the cancer is eliminated (as evidenced by no remission) in a period of no more than several days to about two-three months and does not recur.

23 Claims, 22 Drawing Sheets

(56) References Cited

OTHER PUBLICATIONS

Baruchel S, Ginette Viau. In Vitro Selective Modulation of Cellular Glutathione by a Humanized Native Milk Protein Isolate in Normal Cells and Rat Mammary Carcinoma Model. Anticancer Research, 1996;16:1095-1100.

Clinical Trial Status of Investigational Therapy Multikine (Leukocyte Interleukin, Injection). Feb. 9, 2016 http://www.cel-sci.com/multikine_uses_efficacy_and_clinical_trial_status.html.

Collagenase Drug Information. Medicare Drug List, Jul. 2014 http://medicaredruglist.net/11948/collagenase.html.

Cook JA, et al. Cellular Glutathione and Thiol Measurements from Surgically Resected Human Lung Tumor and Normal Lung Tissue. Cancer Research, 1991;51:4287-4294.

Douglas DM, et al. Effect of Alcide, A New Antimicrobial Compound, on Leukocyte Chemotaxis, in Vitro. Presented at FASEB Meeting, Washington, D.C. Apr. 1, 1987.

EPA. Toxicological Review of Chlorine Dioxide and Chlorite. 2000.

Liotta LA, et al. Role of collagenases in tumor cell invasion. Cancer Metastasis Rev, 1982;1(4):277-288.

Mahvi DM, et al. Intratumoral injection of IL-12 plasmid DNA—results of a phase I/IB chlinical trial. Cancer Gene Therapy, 2007;14:717-723.

Ortega AL, et al. Glutathione in Cancer Cell Death. Cancers, 2011;3:1285-1310.

Oxygen Therapy. Www.cancer.org Jul. 2014.

Pegg AE. Polyamine Metabolism and its Importance in Neoplastic Growth as a Target for Chemotherapy. Cancer Research, 1988:48:759-774.

Polyamines metabolism in regulated normal and abnormal cellular functions. Apr. 2014, http://www.weizmann.ac.il/molgen/Kahana/polyamines.

Redding WR, Booth LC. Effects of Chlorhexidine Gluconate and Chlorous Acid-Chlorine Dioxide on Equine Fibroblasts and *Staphylococcus aureus*. Veterinary Surgery, 1991;20(5):306-310.

Sarin PS, et al. Inactivation of Human T-Cell Lymphotropic Retrovirus (HTLV-II) by LD. The New England Journal of Medicine, 1985; p. 1416.

Simmons PA, et al. Effects of an Experimental Contact Lens Disinfectant on Rabbit Corneal Epithelium Cultures. Optometry and Vision Science, 1991;68(5):369-373.

Abdel-Rahman, et al. Metabolism and Pharmacokinetics of alternate drinking water disinfectants. Environmental health Perspectives, 1982;46:19-23.

American Cancer Society. Questionable methods of cancer management: hydrogen peroxide and other hyperoxygenation therapies. C A Cancer J Clin, 1993;43:47-56.

Alarcon RA. Anticancer system created by acrolein and hydroxyl radical generated in enzymatic oxidation of spermine and other biochemical reactions. Med Hypotheses, 2012;79(4):522-530 A.

Bachrach U. Polyamines and Carcinogenisis. Scientific Journal of the Faculty of medicine in Nis, 2012;29(4):165-174.

Balendiran GK, et al. The role of glutathione in cancer. Cell Biochemistry and Function, 2004;22(6):343-352.

Barber TL. Research Veterinary Medical Officer. Research report. US Dept of Agriculture, Science and Education Administration. Agricultural Research Western Region. Arthropod-borne Animal Diseases Research. Denver, CO, Oct. 3, 1980.

Bremnes RM, et al. The role of tumor stroma in cancer progression and prognosis: emphasis on carcinoma-associated fibroblasts and non-small cell lung cancer. J Thorac Oncol, 2011;6(1):209-217.

Cagan K. Research Report. Naples Laboratories Microbiologists, Long Beach California. Dec. 1, 1979.

Carlton BD, et al. Reproductive effects in Long Evans rats exposed to chlorine dioxide. Environ Res, 1991;56(2):170-177.

Colombo MP. Amount of Interleukin 12 available at the tumor site is critical for tumor regression. Cancer Res, 1996;2531-2534.

Contreras E Sr. Contreras metabolic integrative therapy research. Chapter 5: oxidizing cancer to death. Oasis of Hope Hospital Integrative Regulatory Therapy Research. www.oasis ofhope_com/irt_ch5_oxidizing_cancer.php.

Curley SA, et al. Nonsurgical therapies for localized hepatocellular carcinoma: Radiofrequency ablation, percutaneous ethanol injection, thermal ablation, and cryoablation. Wolters Kluwer Health, Jul. 2014.

Danila M, et al. Percutaneous Ethanol Injection Therapy in the Treatment of Hepatocarcinoma—Results Obtained form a Series of 88 Cases. Dept Gastroenterology and Hepatology, Univ of Medicine and Pharmacy Timisoara, Romania. J Gastroinstin Liver Dis, 2009;18(3):317-322.

Danish-Chinese Centre for Protease and Cancer. The National Science Foundation of China. The Danish National Research Foundation. Proteases and Cancer. www.proteaseandcancer.org Apr. 26, 2014.

Degruyter W. Gene therapy—induced by polyamines. ACTA Facultatis Medicae Naissensis, 2012;29(4):172.

Distefano JF, et al. Role of Tumor Cell Membrane-bound Serine Proteases in Tumor-induced Target Cytolysis. Cancer Research, 1982;42:207-218.

Douglas DM, et al. Mechanism of action of a potential wound-healing compound, Alcide. Presented at Second international Symposium on Tissue Repair Biological and Chemical Aspects. May 13, 1987.

Estrela JM, et al. Glutathione in cancer biology and therapy. Critical Reviews in Clinical Laboratory Sciences, 2006;43(2):143-181.

Fartoux L, et al. Treatment of small hepatocellular carcinoma with acetic acid percutaneous injection. A single French Center experience. Gastroenterologie Clinique et Biologique, 2005;29(12).

Fransen MF, Arens R. Local targets for immune therapy to cancer. Int J Cancer, 2013;132:1971-1976.

Frei B, Lawson S. Vitamin C and cancer revisited. Proceedings of the National Acadamy of Sciences, 2008;105(32).

Gerner EW, Meyskens FL Jr. Polyamines and cancer: old molecules, new understanding. Nature Reviews Cancer, 2004;4:781-792.

Gibellini L, et al. Interfering with ROS Metabolism in Cancer Cells: The Potential Role of Quercetin. Cancers, 2010;2(2):1288-1311.

Halliwell B, et al. Hydrogen Peroxide in the Human Body. GAIA Organics. FEBS Letters, 2000;486(1) Federation of European Biochemical Societies.

Hesselink TL, et al. The science behind the treatment. On the mechanisms of toxicity of chlorine oxides against malarial parasites—an overview. Genesis II, Costa Rica. Sep. 6, 2007. genesis2costarica.org/science-of-chlorine-dioxide/.

Kenyon A, et al. Controlled wound repair in guinea pigs, using antimicrobials that alter fibroplasias. Am J Vet Res, 1986;447(1).

Kenyon K, et al. Comparison of antipseudomonad activity of chlorine dioxide/chlorous acid containing gel with commercially available antiseptics. Am J Vet Res, 1986;47(5).

Khamis ZI, et al. Active roles of Tumor Stroma in Breast Cancer Metastasis. Int J of Breast Cancer, 2012, Article ID 574025, 10 pages. dx.doi.org/10.1155/2012/574025.

Lanham JW, Section Chief, Life Sciences. Research report. McDonnell Douglas Astronautics Company, St. Louis Division. Jan. 5, 1981.

Li H, et al. Tumor microenvironment. The role of the tumor stroma in cancer. Journal of Cellular Biochemistry, 2007;101(4):805-815.

Lin SM, Lin DY. Percutaneous Local Ablation in Small Hepatocellular Carcinoma. Chang Gun Med J, 2003;26:308-314.

Liou GY, Storz P. Reactive oxygen species in cancer. Free Radic Res, 2010;44(5):479-496.

Lubbers J, et al. Effects of the chronic oral administration of chlorine dioxide, chlorate, chlorite and chloramines to normal healthy volunteers; A controlled study. The Pharmacologist, 1980;22(3):171.

Lubbers JR, et al. Controlled clinical evaluations of chlorine dioxide, chlorite and chlorate in man. Environmental Health Perspectives, 1982;46:57-62.

(56) References Cited

OTHER PUBLICATIONS

Luk GD, Casero RA Jr. Polyamines and cancer cells. Adv Enzyme Regul, 1987;26:91-105.
Cerven DR.. Vaginal toxicity in rabbits. Project #MB 99-7837.22 Spinnerston, PA. Jan 4, 2000.
Mohammad A, et al. Clinical and microbiological efficacy of chlorine dioxide in the management of chronic atrophic candidiases: an open study. International Dental Journal, 2004;54:154-158.
Ohnishi K, et al. Prospective randomized controlled trial comparing percutaneous acetic acid injection and percutaneous ethanol injection for small hepatocellular carcinoma. Hepatology, 1998;27(1):67-72.
Ruttimann J. Macrophages and nitric oxide: A deadly combination. The Journal of Experimental Medicine. JEM Home, 2008;204(13):3057.
Scatina J, et al. Pharmacokinetics of Alcide, a Germicidal compound on rat. Journal of Applied Toxicology, 1983;3(3):150.
Schultz S, et al. Treatment with ozone/oxygen-pneumoperitoneum results in complete remiof rabbit squamous cell carcinomas. Int J Cancer, 2008;1229(19):2360-2367.
Soda K. The mechanisms by which polyamines accelerate tumor spread. Journal of Experimental and Clinical Cancer Research, 2011;30:95.
US Department of Health and Human Services. Toxicological profile for chlorine dioxide and chlorite. Sep. 2004, 141 pages.
Vaupel P. The Role of hypoxia-induced Factors in Tumor Progression. The Oncologist, 2004;9(5):10-17.
Waldner MJ, et al. Interleukin-6—A key regulator of colorectal cancer development. Int J Biol Sci, 2012;8(9):1248-1253.
Walker H, et al. Topical use of sodium chlorite-lactic acid gel in pseudomonas burn wound sepsis. US Army Institute of Surgical Research, Fort Sam Houston TX. 1981.
Weiss SJ, et al. Oxidative autoactivation of latent collagenase by human neutrophils. Science, 1985;227(4688):747-749.
Witold Lasek, Interleukin 12: "still a promising candidate for tumor immotherapy". Cancer Immunol Immunother, Jan. 2014;63(5):419-435.
Brinckerhoff CE, et al. Interstitial Collagenases as Markers of Tumor Progression. Clinc Cancer Res, 2000;6:4823.
Mahoney DJ, et al. Virus Therapy for Cancer. Scientific American, 2014;311:54-59.

\* cited by examiner 24 hours after treatment, the tumor has been completely removed leaving granulation and necrotic subcutaneous tissue 72 hours after treatment the wound is healing 5 days after treatment the wound margins continue to contract and no evidence of remaining tumor material is seen

FIGURE 21

Table 1- Toxicity of the Present Composition by Injection (Mouse)

| Mouse # | Organ Injected | Dilution | Dose | Time of injection | Evaluation time | Result |
|---|---|---|---|---|---|---|
| 1 | liver | 25% 100ul INtume : 300ul saline | 50ul | 10:30 AM | 30 min | No sign of toxicity to organ or mouse |
| 2 | spleen | 25% 100ul INtume : 300ul saline | 50ul | 10:36 AM | 5-10 min | Mouse over anesthetized by accident and passed. No initial signs of toxicity noted. |
| 3 | kidney | 25% 100ul INtume : 300ul saline | 50ul | 10:55 AM | 30 min | No sign of toxicity to organ or mouse |
| 4 | spleen | 25% 100ul INtume : 300ul saline | 50ul | 10:45 AM | 20 min | No sign of toxicity to organ or mouse |
| 1 | liver | 50% 100ul INtume : 100ul saline | 50ul | 11:00 AM | 30 min | No sign of toxicity to organ or mouse. This mouse received 2 doses. |
| 5 | liver | 100% INtume | 50ul | 11:12 AM | 30 min | No sign of toxicity to organ or mouse. |

FIGURE 22

Table 2- Injection of Methylene Blue

| Mouse # | Organ Injected | Dilution of MB | Dose | Time of Injection | Evaluation Time | Result |
|---|---|---|---|---|---|---|
| 3 | kidney | 100% | 50ul | 11:25 AM | 10 min | Dye filled entire kidney when injected and then came out. Dye did not spread throughout the body but did saturate the entire kidney. The dye got into the urine. |
| 1 | spleen | 100% | 50ul | 11:32 AM | 5 and 10 min | Injection instantly turned the whole spleen blue. At 5 minutes the messentary vein is taking up the dye, but none of the other organs have. At 10 min more of the other organs turned blue. Spleen looks saturated with dye when cut in half. |
| 5 | liver | 100% | 100ul (50ul shallow, 50ul deep) | 11:43 AM | 7 min | A lot of leakage into area during injection. Liver doesn't look completely blue prior to cutting open. After cutting open the blue was found only at the injection site but remainder of liver was not blue. |

METHOD AND COMPOSITIONS FOR TREATING CANCEROUS TUMORS

RELATED APPLICATIONS

The present application claims the benefit of priority of provisional application Ser. No. 62/317,330 filed Apr. 1, 2016, entitled "A New Method for Promoting Tumor Necrosis" and provisional application Ser. No. 62/337,073, filed May 16, 2016, of identical title, both of which applications are incorporated by reference in their entirety herein.

FIELD OF THE INVENTION

The present invention relates to the use of chlorine dioxide compositions for treating cancerous tumors. The present invention relates to compositions and methods for treating cancerous tumors, including naïve, metastatic and recurrent cancers. The compositions comprise chlorine dioxide or chlorine dioxide complexes in an effective amount, which is injected into the cancerous tumor at least once, preferably into the tumor so that the tip reaches the opposite side at many points of the inner tumor wall. The chlorine dioxide compositions are administered (preferably, by injection) directly into the cancerous tumor and the resulting tumor is effectively eliminated from the patient or subject over a period of one to several days to a few weeks, often after a single injection or multiple injections at one time into the tumor. Often, an initial injection or multiple injections at one time are sufficient to dissolve the cancerous tumor. Often the cancer is eliminated (as evidenced by remission) in a period of no more than several days to about two-three months and does not recur.

BACKGROUND AND OVERVIEW OF THE INVENTION

Polyamines (PA) are organic cations found in all organisms, and their synthesis occurs in the cytoplasm of all cells. Polyamine research dates back several centuries; in 1678 Van Leewenheuk saw crystals in semen that were later identified as spermine.

The following text points out several possibilities and chemical pathways in which "Intume" chlorine dioxide intervention can destroy tumors and prevent proliferation of cancer cells. Removing all polyamines is a main objective, but at the same time neutralizing other systems that aid the neoplasm also appears to be important. Chlorine dioxide (ClO2), a strong oxidant, can safely be injected into a subject's body, including a tumor, although the compound has not yet been utilized as a cancer treatment in this manner. ClO2 is highly penetrating, and generally considered non toxic—as demonstrated by its application in deep wounds, $3^{rd}$ degree burns, and use in oral and topical diseases.[i,ii,iii,iv,v,vi,vii,viii]

Cancer cells are rich in polyamines which is necessary for survival and growth of tumors.[ix] Capacity of cancer tissue to produce abundant PA likely contributes to cancer cell's higher growth rates.ix,[x] High concentrations of PA enhance cancer cells to invade, and is associated with less apoptosis and increased expression of the genes affecting metastasis.ix,[xi] The association of increased polyamine synthesis and cancer was first reported in the late 1960s. Interest in targeting polyamine metabolism as a potential strategy for cancer chemotherapy was stimulated in the early 1970s.[xi] From the late 1970s and throughout the 1980s the endogenous polyamine inhibiting compound, difuoromethylornithine (DFMO), was actively evaluated as an anticancer drug. Unfortunately, the attempt at inhibition of PA synthesis, as well other chemical intervention, has proven to be generally ineffective as an anticancer strategy in clinical trials.[xi] Surprisingly, similar experiments were successful in in vitro and on animal models. Inhibition of polyamine by DFMO in animal experiments reduced tumor growth and decreased the amount of metastasis, resulting in prolonged survival of the animals.ix With the introduction of the present "Intume Oxidant," polyamine synthesis will be halted by ClO2 oxidation of existing PA, along with oxidation of PA precursor molecules, arginine and ornithine. In addition, the thiol, ODC, which mediates PA manufacture within cancer cells by reducing DFMO, will also be oxidized by ClO2.

PA concentrations in blood and urine of cancer patients reflect the levels of PA synthesis in cancer tissues.[xi] Concentrations in the blood may vary widely in healthy individuals; however, cancer patients with increased PA levels in blood or urine are reported to have more advanced disease and worse prognosis.[xi,xii] Increases can also predict relapse of the disease.[xi]

Chlorine dioxide will oxidize polyamines, and the resultant oxidation products, hydrogen peroxide and aldehydes, are both highly toxic to the cancer cell itself.[xiii,xiv,xv] Normal cells contain much smaller amounts of PA and will not be affected as much.[xiv] The increased hydrogen peroxide produced by the oxidation can cause cancer cells to undergo apoptosis, pyknosis, and necrosis[xvi]—some of the physical controls the body uses to remove cancer cells. The chemical result of chlorine dioxide oxidation may be similar to the endogenous hydrogen peroxide's removal of the cancer cell. Normal cells are considerably less vulnerable to peroxide, or any oxidation, due to the greater amount of catalase reducing agent in the non-transformed cell.[xvii]

Direct injection of Intume ClO2, a relatively non toxic oxidant, would better substitute the body's natural intracellular hydrogen peroxide. For general topical use on disease, peroxide cannot be applied to bad wounds, due to its cytotoxicity.[xviii] Chlorine dioxide on the other hand, when used to treat disease, is an aid to healing and prevents scarring.[xix,ii] It is often used by veterinarians on bad infections,vi and applied experimentally on people for non healing wounds like diabetic ulcers. Twenty five years of difficult internal applications has indicated no adverse events,[vi] except that of oxidizing red blood cells. No other antiseptic—for example, chlorhexidine, hydrogen peroxide, hypochlorite, or silver ions, are acceptable for disinfection of deep wounds.

Amine oxidase, an extracellular oxidant and biological regulator, also oxidizes polyamines yielding cytotoxic products. Cancer cells with their high PA content would be inactivated preferentially by a strong oxidizing agent. When amine oxidase was microinjected into cultured fibroblasts of chick or rat embryos, a slight temporary inhibition in DNA and protein synthesis was observed.[14] But after these normal fibroblasts were transformed by virus, they were more susceptible to the injected enzyme than the normal cultures. Similarly, when the oxidase was injected into tumor bearing animals, there was a "remarkable decrease" in tumor growth.[xiv]

Another endogenous oxidizing agent, nitric oxide, is also involved in destroying tumor cells. In this case the NO oxidant is released by macrophages.[xx]

ClO2 will oxidize thioles, phenols, purines, secondary and tertiary amines; also tyrosine, tryptophan, and histidine.[xi] Most heavy metals are oxidized also. All of these compounds are involved with tumor metabolism. Inhibiting these and key enzymes will disrupt tumor proliferation.$^{xii}$ Almost all sulfur bearing molecules can be oxidized by ClO2 if the sulfur is not in the form of sulfate Elevated rates of reactive oxygen species (or ROS) have been detected in almost all cancers.$^{xxi,xxii}$ They promote many aspects of tumor development, DNA damage, growth, proliferation and angiogenisis.$^{xxi,xxii}$ These highly reactive oxidants will be neutralized in an oxidation/reduction reaction with ClO2, similar to the better known in vitro chemical effect of chlorine dioxide with common oxidants, hypochlorite, ozone, or peroxide. Direct contact of ClO2 in the cell would overcome the cancer increasing ROS effect.

Cancer cells in the process of synthesizing polyamines is also associated with increased production of proteinases such as serine proteinase, metalloproteinases, cathepsins, and plasma activator, all of which tend to degrade surrounding tissue, permitting cancer cell passage.ix Many investigators have been concerned with enzyme activity disrupting this important extra cell matrix (ECM),$^{xxiii}$ and also the activity in the surrounding stroma connective tissue. Some proteases also catalyze activation of growth factors and thus regulate growth of primary tumors as well as permit metastases.$^{xxiv}$ ClO2 should easily neutralize sulfur bearing proteases involved.

Tumor cells produce collagenase proteolytic enzyme which occurs at a higher level than in corresponding benign tissues.$^{xxv}$ The ability of transformed cells to invade surrounding tissues strongly depends on collagenase (MMP) since this particularly active proteinase degrades the structural components of the ECM and cell-cell adhesion molecules. The first evidence that collagenase played a role in preventing cell invasion is derived from in vitro experiments in which addition of collagenase inhibitors blocked tumor escape into the ECM.$^{xxv}$ Collagenase, like other sulfur bearing enzymes is easily oxidized.$^{xxvi}$ The enzyme is also inactivated at the low pH of Intume.

Cancer cells can take up PA from their surroundings, and also export PA to the extracellular space as well.$^{xi}$ Because of this, adding Intume solution surrounding the tumor may be a reasonable anti neoplastic action. Increased PA uptake by immune cells results in reduced cytokine production of tumor necrosis factor, otherwise needed for antitumor activities.ix Adhesion molecules are also affected by this secreted PA.ix For cancer cells to invade, favorable chemical interactions must take place between cancer cell and the stroma framework.$^{xxvii,xxviii,xxix}$ Several papers describe this signal pathway as "crosstalk,"$^{xxviii}$ and interplay between the two adds to the progression of tumors and metastasis. Intume chemical action would likely interrupt this neoplastic link by targeting both tumor and surrounding stroma.

The cytokine, Interleukin 6 (IL-6), a mediator of inflammation, steadily increases in the blood as cancers become more life threatening.$^{xxx}$ I1-6 is regarded as an important tumor promoting factor in many types of human cancers.$^{xxx}$ The compound contains disulfide bonds, which will be oxidized by ClO2.

Glutathione reducing agent serves important functions within cells, but its rapid synthesis in tumor cells is also associated with high rates of cellular proliferation and cancer growth.$^{xxxi}$ Removing glutathione by oxidation would then inhibit this tendency of cancer spread, as well as, indirectly enhance the effectiveness of subsequent standard therapy. Radiation and chemotherapy depend on the cidal oxidation by hydrogen peroxide which is removed by glutathione$^{xxxi,xxxii}$ Depletion of glutathione appears therapeutically effective only when low levels can be achieved,$^{xxxii}$ and several drugs have been tried in the past for reducing glutathione, but found to cause damage in normal tissue.$^{xxxi,xxxii}$ However, excess ClO2 in and around the cancer cell or nodule would not be expected to have a particularly adverse effect on surrounding normal tissue or organs as do other anticancer compounds, except for its oxidation of hemoglobin. Previous experience has shown that ClO2 does not irritate neighboring tissue when used as an antiseptic on bad wounds and diseases. In tissue culture experiments, highly diluted chlorine dioxide is able to kill bacteria within a normal cell without injury to the cell itself.$^{xxxiii,xxxiv,xxxv,xxxvi}$ Chlorine dioxide is a good penetrant, soluble in water, oil, serum, saliva, and in a wide range of pH. As an example, when applying ClO2 as an antiseptic topically, the oxidant treats fungus of the nail, a difficult disease to cure, by penetrating the nail and tissue around the nail. When applied to warts, the thickened tissue is penetrated, killing the papilloma virus within. Ring worm on cats is successfully treated by apparently entering the hair follicles and killing the fungal spores; surprisingly, no other topical medication works well for ring worm on cats. When placed on rats in a 60% of the body $3^{rd}$ degree burn, no toxicity was indicated.$^{i}$ If ClO2 is placed on a wound for disinfection, the metabolized oxidant products, chlorite and chloride, are absorbed in the body and are eliminated rapidly in the urine.$^{xxxvii,xxxviii,xxxix,xl}$ Many ingestion studies by the EPA in animals and humans have been performed with ClO2 displaying few, if any, adverse effects.$^{xxxviii}$ Chlorine dioxide is not the first anticancer compound to be injected into tumors, but probably the only percutaneous such compound relatively safe on non transformed tissue, and suitable for contacting internal organs. For about 25 years, 50% acetic acid, and 100% ethyl alcohol, has been injected into animal and human liver tumors.$^{xli}$ Both these compounds are normally considered corrosive and irritating, but nevertheless they are effective in ablating liver cancer cells with low morbidity—at least in the short run. It is surprising that highly toxic treatments would be utilized on liver cancers since a majority of these patients have underlying liver disease and are at high risk for recurrent disease and of progression to liver failure.$^{xlii}$ In one fairly large study evaluating 102 liver cancer patients where acetic acid was used to necrotize cancer cells, it states, "Even in well selected patients, the high rate of recurrence of multifocal hepatocellular carcinoma underline the limits of this method as well as all other percutaneous strategies."$^{xliii}$ In any case, because of Intume's relatively low toxicity, liver tumors larger than 3 cm might be treated with curative intent, or just as a palliative therapy not possible now. Further, Intume intervention is not specific to one type of tumor as is the case with acetic acid and ethyl alcohol on liver tumors. ClO2 treatment could also be described as the removal of vital constituents, and not just gross obliteration of tissue that occurs with heat, radiation, or strong chemicals such as acetic acid.

The history of putting oxygen releasing substances into the body follows several tracks.$^{xliv,xlv}$ Interest in ozone dates back to the mid 1800s in Germany, where it was claimed to purify the blood. One of the earliest accounts of the medical use of hydrogen peroxide was a short article in 1888 in the Journal of The American Medical Association.$^{xliv}$ A physician described a case where peroxide was useful in removing pus from the nose and throat of a child with diphtheria; and also recommended using peroxide for cancer of the womb—as cleanser, deodorizer, and stimulator of healing.[xliv] During World War 1, doctors used ozone to treat wounds, trench foot, and the effects of poisonous gas. In the 1920s, ozone and peroxide injections were used experimentally to treat the flu. In 1920 peroxide injections were used on patients during an epidemic of viral pneumonia.

Alternative Medicine practitioners claim that cancer cells thrive in low oxygen environments, and adding oxygen to the body creates an oxygen rich condition in which cancer cells cannot survive. Use of ozone or oxygen in small amounts under controlled conditions for treating limited parts of the body has shown some success in mainstream medical research.[xliv,xlv] Another "alternative" theory approach involved hydrogen peroxide and also chlorine dioxide taken by mouth or injected into a vein—all well short of FDA aegis. For good or ill, practitioners promote oxygenation for use rectally, vaginally, as a nasal spray, as a soak, and as ear drops.

With the Intume ClO2 therapy proposed now, many types and sizes of tumors have a good chance to be destroyed; a welcome option when other methods of removal cannot be tolerated. Injection by Intume would be particularly valuable, for example, when a small part of the tumor is in intimate association with nerves, vessels or cartilage, and complete removal of the tumor not possible by surgery; or a gratifying substitution to avoid unpleasant side effects of present therapies. Just slowing the growth of a large recalcitrant tumor can extend someone's life, or quality of life. Ethanol injection therapy and radio frequency ablation have been used on liver tumors as a large as 10 to 12 centimeters in diameter as palliative therapy, in order to increase patient survival rate.[xlvi]

A direct approach into the tumor with Intume would probably not cause adverse events elsewhere in the body as did DFMO in human trials. In a Review Article comparing therapies for liver tumors, "Although surgical resection is generally preferred for curative ablation, the long term survival rates following resection are no better that those following local ablation."[43,xlvii] For many years research on cancer has largely been ruled by the view that genetic mutations drive tumor growth. However, cancer may be as much a disease of disturbed microenvironment as it is a result of disturbed genes.[xlviii] The tumor microenvironment composed of non-cancer cells and their stroma has become recognized as a major factor influencing the growth of cancer.[xxvii] Alterations of cell shape and of the cell's surroundings may actually precede the onset of tumors and even initiate the disease.[xlviii] The area around a particular surgical site could be saturated by oxidative Solution with the prospect of preventing neoplasm transformation.

Tumors may be injected by ultrasound guided needles similar to guided biopsy probes, or by CD fluoroscopy. Conceivably metastasized tumors might be treated with a needle injection; and in the case of a very large tumor, many injections can be made in a single therapy session. The hypoxic core of the tumor may be an ideal place to inject chlorine dioxide. The strong oxidant would no doubt disrupt or neutralize the hypoxic area already weakened by lack of blood flow. Hypoxia, a common condition in cancer tissues, exerts a strong pressure on cells to separate from the tumor cluster and migrate into circulation.[ix]

By injecting Intume oxidant, and thereby removing the natural reducing molecules, catalase and glutathione within and around the cancer cell, tumors could then be more easily treated, as stated previously, by relatively low doses of oxidizing therapies such as radiation and chemotherapy.[xi xlix]

Both DFMO and NSAIDS taken orally by animals have been shown (in animals only) to reduce cancer. These compounds treat neoplastic disease each by different chemical route.[xi] They also worked additively in inhibiting cancer of the colon and intestine in murine models.[xi] Since Frontier's Intume would probably remain active for only a few hours after each injection, adding these two options, to the patient as well as others, on an oral ongoing basis, could conceivably remove weakened or nascent tumor cells remaining. Although the Intume oxidative interaction may by relatively short, the kind and variety of new molecules produced in the debris field could likely recruit an immune response for some time.[l] Conceivably there may be a salutary effect on distant metastasis, as well. Athymic mice, however, now proposed for the first tumor studies, would not have any additive protective immune ability.

An immunosuppressive rebound that sometimes takes place in human anti cancer therapy may not as easily occur in the case of Intume treatment since too much of the transformed cell and associated environment will be disrupted. There is a reasonable chance also that the great number of new cellular particles and molecules, along with an influx of T cells and neutrophils, would choke off blood vessels and the tumor's nutrient supply.[l]

In 1978, the present inventor was the first to patent the idea of placing ClO2 on the body to cure disease. Since then, more than 200 patents have been issued for animal topical application. Applications varied from scratches to deep wounds, from fungus infections to viral, and bacterial. and yeast, from fungus of the nail to sun keratoses on the scalp. Ear infections, and sinus infections. From mouthwash cleaning to bad acne infections. Colds and sore throats and wart removal and deep wounds.

Much to the chagrin to the FDA, people also drank ClO2 for internal applications like intestinal and stomach diseases and also malaria, and even autism. These applications are quite doubtful and even dangerous and are packaged and sold from Mexico. ClO2 was used to purify the blood even though ClO2 can not exist in blood and was never found in the blood. It is too strong an oxidizing agent. Blood is filled with reducing agents that would immediately neutralize ClO2: glutathione, catalase, super oxide dismutase, vitamins, minerals, to name a few. One of the well known drawbacks to the topical application of ClO2 is the need to measure two parts first, mix them, and usually wait a few minutes, before applying. Also in the usual course of ClO2 application the pH needs to be quite acidic, normally below 3 in order to release the needed amount ClO2 from the salt sodium chlorite. Many times the pH was too low for wound or disease application. Finally ClO2 can not be easily stored as it is a gas and must be released just before use. Since ClO2 release from chlorite is continuous so that the concentration is a moving target when applying to a disease.

BRIEF DESCRIPTION OF THE INVENTION

The present invention relates to a method of treating cancer, in particular a cancerous tumor in a patient or subject in need comprising administering by direct injection into the tumor, but alternatively into multiple sites within the tumor including the core, an effective amount of chlorine dioxide, including a chlorine dioxide complex. The treatment often occurs pursuant to a single treatment with the cancerous tumor simply dissolving or dissipating over a course of several days without further treatment or may occur over multiple treatments over a period of a few days to several weeks or with injections performed daily or less often depending on the patient response. Often, the tumor will disappear after a single treatment, in a few days to a week or so, but occasionally more than one treatment is required over a several day or several week period or more. The result is usually complete remission, even in difficult to treat cancers and no metastasis or recurrence of the cancer occurs.

The chlorine dioxide for use in the present invention may be prepared from two parts, i.e., from a salt of chlorite such as sodium or potassium chlorite and an acid, preferably an acid such as a salt of bisulfate, phosphoric acid or a stronger acid such as HCl or $H_2SO_4$, among others, including an organic acid (e.g., a $C_2$-$C_{20}$ organic acid such as acetic acid, propionic acid, lactic acid, salicylic acid, etc. which may be less preferred, depending on the embodiment). Sometimes a disrproportionation agent may be added and also the resulting chlorine dioxide solution may be optionally stabilized with an effective amount of urea to provide storage stable chlorine dioxide solutions. In certain embodiments, a two part composition comprising a salt of chlorite and optionally a disproportionation agent in a first part composition is combined with an acid in a second part composition is used.

In an alternative embodiment to the two part composition described above, a one part storage stable chlorine dioxide solution may be prepared by first combining the salt of chlorite with urea or a urea-like compound such as thiourea or monomethylurea and then acidifying the mixture to produce stabilized chlorine dioxide (stabilized with urea). The total amount of ingredients are not critical, as any amount will work, but preferably the urea is included in an amount (by weight) about the same as or greater than the chlorite. Using the same ratio of chlorite and urea however, provides an efficient use of the starting ingredients. In this embodiment, a solution of a salt of chlorite (e.g. at about 2% to about a 15% by weight aqueous solution, more often a 4% to about 10% solution, even more often about a 5-8% solution, even more often about 6-7% solution) is mixed with a urea solution at about 10-35% by weight aqueous solution, more often about 15-30% solution, even more often about 15% to about 25%, or 20% solution, for a period sufficient to thoroughly mix the components and to this solution of a salt of chlorite and urea is added an acid to lower the pH of the solution to less than 4.5, preferably less than 4.0, often about 3.0 or less or even 2.5 or less and the solutions is mixed thoroughly, often for several hours or longer. Left standing, the solution turns clear after a sufficient period of time, for example, about a day or so and the resulting chlorine dioxide solution which results is stable and ready to utilize in treating cancerous tumors (as well as numerous other applications). Percentage (%) by weight refers to the fact that the component represents that % by weight of the total solution/final composition which includes that component. The concentration of chlorine dioxide in the solution ranges from about 5 parts per million to about 1,000 parts per million, more often about 10 ppm to about 750 ppm, about 15 ppm to about 500 ppm, about 25 ppm to about 200 ppm, about 35 ppm to about 150 ppm, about 20 ppm to about 100 ppm, about 15 ppm to about 150 ppm. The concentration of chlorine dioxide to be used will depend on the nature of the cancer tumor, its size and location and the patient/subject to be treated. The concentration of urea in the storage stable compositions according to the present invention will preferably range from about 1-50 times the concentration of chlorine dioxide in solution (i.e., about 5 ppm to about 50,000 ppm), preferably about 1-25 times (about 5 ppm to about 25,000 ppm), more often about 2-10 (about 10 ppm to about 10,000 ppm) times the concentration of chlorine dioxide in solution in order to instill stability to the carbon dioxide solution. The storage stable compositions also contain sufficient acid to lower the pH of the composition to less than about 4.5, less than 4.0, 3.5, 3.0, 2.5 and 2.0.

To treat cancer, the composition is administered directly into the cancerous tumor to be treated. Preferably, the composition is taken up into a syringe or other injection device (modification of a syringe may be needed to accommodate gelled formulations) and injected directly into the tumor. The amount used is an effective amount which can range in concentration as discussed above. While it is acceptable to inject the composition directly into the core of the tumor in a single injection, it is often preferred that the composition is injected in several places in the tumor—the composition is favorably injected into as many areas of the tumor as is possible especially at the inner wall of the tumor. Compositions may be injected into the tumor daily, more than once daily, or less than daily, depending on the size and nature of the tumor, the patient/subject response and the effect on the therapy on the tumor, which may be carefully monitored. Treatment is often completed within a period of a day or several days. It may be that several months may be necessary depending upon the size and nature of the cancerous tumor to be treated.

BRIEF DESCRIPTION OF THE FIGURES

FIGS. 1-6 show multiple injections of storage stable chlorine dioxide composition into breast, brain and prostate tumors using the storage stable composition of example 1. In particular, 250 or 300 μL of the example 1 chlorine dioxide solution was injected into the tumors. FIGS. 1-2 show the results of the use of the composition in breast tumor. FIGS. 3-5 show the results in brain tumor. FIG. 6 shows the results in prostate tumor. In each instance the tumor was removed and healing commenced.

FIGS. 7-9 evidences that the brain tumors (U87) in mice were eliminated using the compositions/methods of the present invention (composition at pH 2.5) and the wound healed rather nicely as it evidences almost complete closure (FIG. 9).

FIGS. 10-18 show the results treating exogenous brain tumors in athymic mice. FIG. 10 shows the exogenous brain tumor in an athymic mouse. FIG. 11 shows that one day after injection with the composition of the present invention, the tumor was no longer present. FIG. 12 shows that the healing process has started as indicated by granulation tissue, with some necrosis on the edges, 5 days after the initial injection. FIG. 13 shows more healing several (3) days later. FIG. 14 shows that healing continued 5 days after the photo presented in FIG. 13. FIG. 15 shows that six (6) days later the wound was almost completely closed. FIG. 16 shows that the wound from the elimination of the brain tumor was completely closed in three (3) weeks. FIG. 17 shows that the mouse is completely healed and no tumor re-growth had occurred two months later. FIG. 18 shows the complete healing of the brain tumor from another angle.

FIGS. 19 and 20 show the progression of treatment and healing using the present invention over 5 days. In these figures, 300 μL of the composition of example 1 was injected into the mouse tumor (brain). Some photos in FIGS. 19 and 20 overlap. These figures evidence that after only 5 days of treatment, healing of the tumor is clearly visualized.

FIGS. 21 and 22 show the data obtained from toxicity studies of the present invention in laboratory mice for the present composition (Table 1) in comparison to methylene blue (Table 2).

DETAILED DESCRIPTION OF THE INVENTION

Figure 1:
FIGS. 1-20 show treatment of cancerous tumors using compositions according to the present invention.
Figure 2:
Figure 3:
Figure 4:
Figure 5:
Figure 6:
Figure 7:
Figure 8:
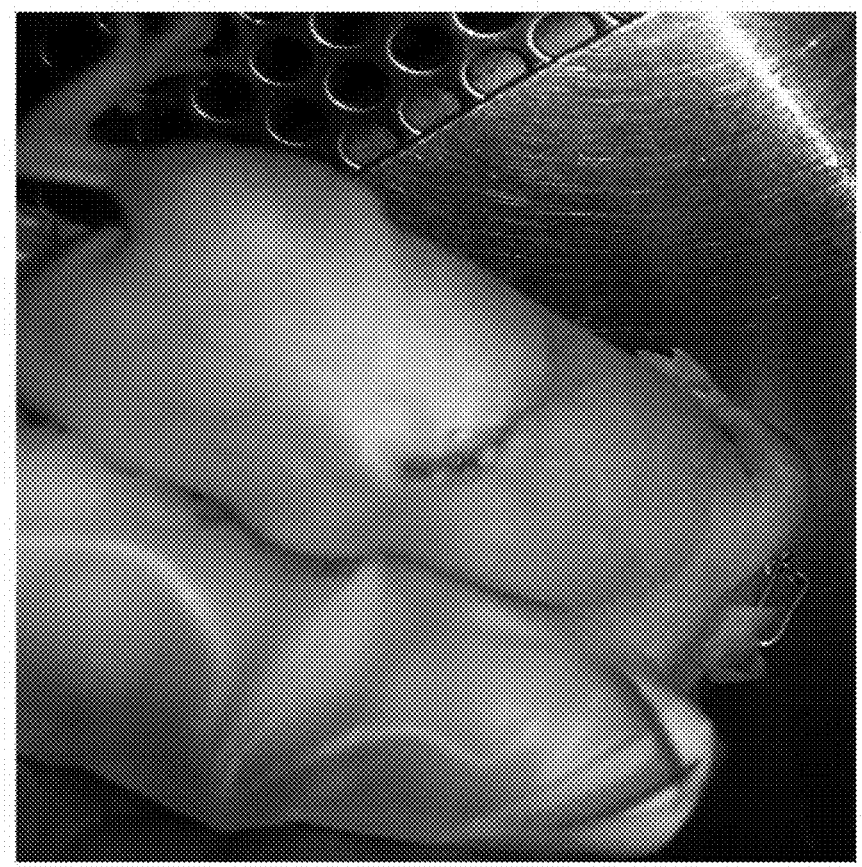
Figure 9:
Figure 10:
Figure 11:
Figure 12:
Figure 13:
Figure 14:
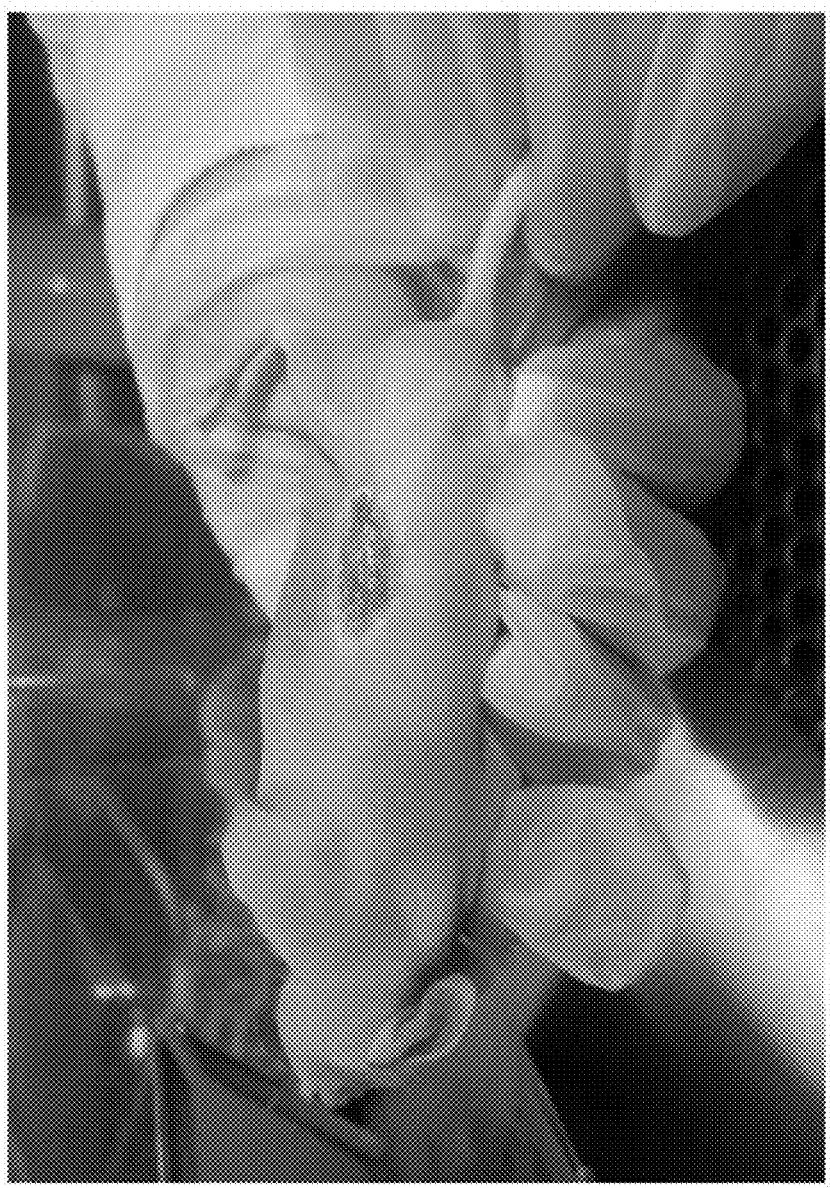
Figure 15:
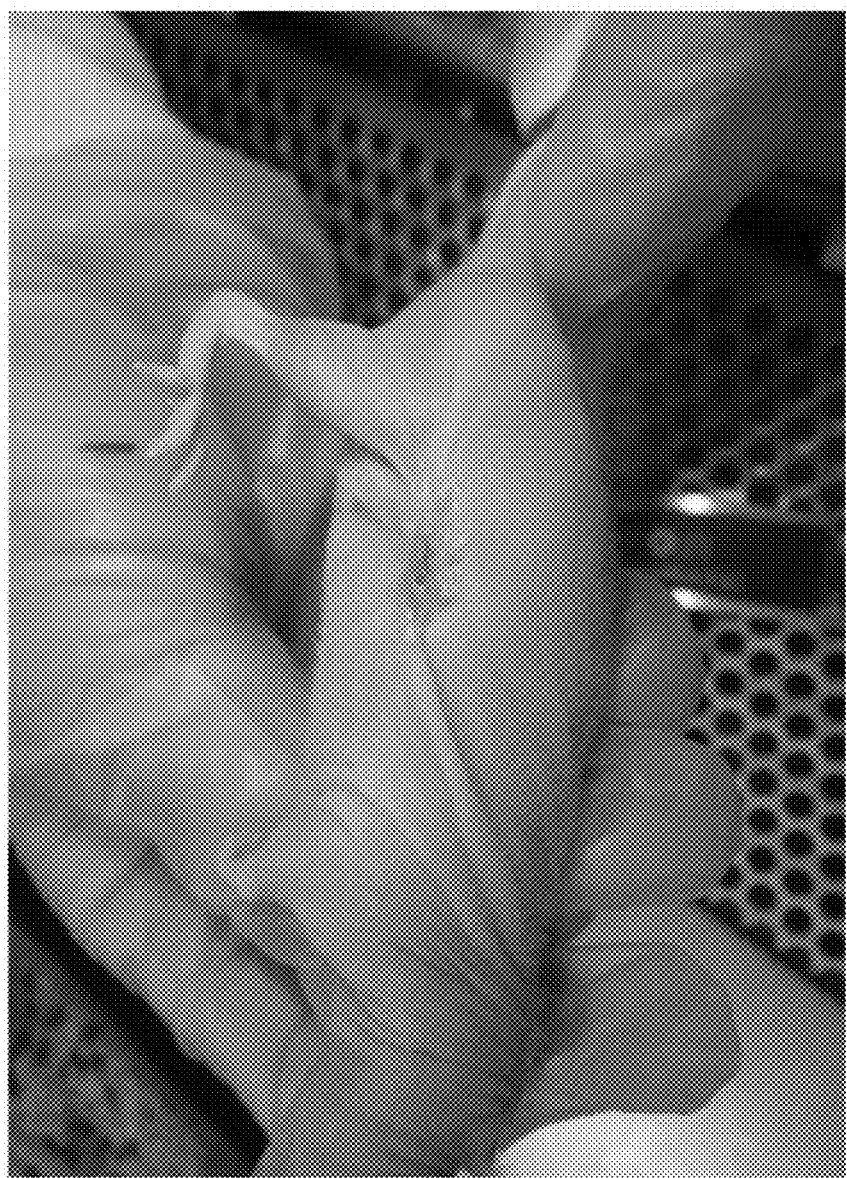
Figure 16:
Figure 17:
Figure 18:

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound", as used herein, unless otherwise indicated, refers to any specific chemical compound disclosed herein and includes pharmaceutically acceptable salts. Within its use in context, the term compound generally refers to a single compound such as an acid, chlorite salt, urea or disproportionation agent.

The term "patient" or "subject" is used throughout the specification within context to describe an animal, generally a mammal and preferably a human, to whom treatment, including prophylactic treatment (prophylaxis such as to avoid recurrence of a cancerous tumor), with the compositions according to the present invention is provided. For treatment of those infections, conditions or disease states which are specific for a specific animal such as a human patient or a patient of a particular gender, such as a human male or female patient, the term patient refers to that specific animal or that gender. Compounds according to the present invention are useful for the treatment, inhibition or prophylaxis ("reducing the likelihood") of cancer, including metastatic and recurrent cancer.

The term "chlorine dioxide complex" or "chlorine dioxide complex composition" refers to a composition which comprises chlorine dioxide, urea and acid having a pH preferably less than 4.5. This composition provides a complex which is preferably prepared by thoroughly mixing a salt of chlorite in aqueous solution with urea (either neat or preferably as a solution), followed by acidifying the solution to a pH of less than about 4.5, 4.0, 3.5, 3.0, 2.5 or even less than 2.0, thoroughly mixing and allowing the final mixture to stand for a number of hours to provide a clear solution of a chlorine dioxide complex as otherwise described herein. The amounts of each of the components are not critical, although salts of chlorite and urea are used preferably at concentrations of about 1:1 to about 10:1, more often about 1:2 to about 1:3.5 as otherwise described herein. This composition is a preferred composition for carrying out the present invention of treating cancerous tumors pursuant to the present invention.

The term "effective" is used herein, unless otherwise indicated, to describe an amount of a compound or composition (most often a stabilized chlorine dioxide composition or stabilized chlorine dioxide complex composition) which in context, is used to produce or effect an intended result, whether that result relates to the inhibition of cancer, including metastatic cancer or the treatment of a subject for secondary conditions, disease states or manifestations of cancer as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer, including the metastasis or recurrence of cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others. Treatment, as used herein, encompasses both prophylactic and therapeutic treatment. It is noted that in preferred embodiments, the present invention provides a very rapid and in many instances complete remission of cancer which does not recur. The term "prophylactic" when used, means to reduce the likelihood of an occurrence or the severity of an occurrence within the context of the treatment of cancer, including cancer metastasis as otherwise described hereinabove. Prophylaxis often refers to the treatment of a cancer patient in remission (the naïve, metastatic or recurrent cancer is in remission) and the composition is used to reduce the likelihood of a recurrence or further recurrence of cancer.

The term "tumor" is used to describe a malignant or benign growth or tumefacent. Cancerous/malignant tumors are tumors which are the subject of the treatment of the present invention.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis. The cancer may be "naïve", metastatic or recurrent and includes drug resistant and multiple drug resistant cancers, all of which may be treated using compounds according to the present invention.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of malignant neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, thyroid and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine/endometrial cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "salt of a chlorite" or "chlorite salt" is used throughout the specification to describe a salt of chlorite which is readily soluble in an aqueous system and which readily dissociates into chlorite anion and counterion (generally, metal). Two particularly preferred salts of chlorites for use in the present invention include sodium chlorite and potassium chlorite.

The term "chlorine dioxide composition" is used throughout the specification to describe a composition containing an effective amount of chlorine dioxide, however made, which can be used to treat cancerous tumors herein. Chlorine dioxide compositions may be made by combining a chlorite salt solution with an acid solution, optionally in the presence of a disproportionation agent. Preferably, chlorine dioxide compositions pursuant to the present invention are directed to storage stable compositions which are prepared, as otherwise described using a chlorite salt solution, a urea solution and separately an acid solution to form a chlorine dioxide complex in solution. The chlorine dioxide composition may be formulated as a liquid solution or as a gelled product using an effective amount of a gel, especially glycerin.

The term "acid" is used throughout the specification to describe protic acids, i.e., acids that release hydrogen ions in solution. Acids for use in providing chlorine dioxide compositions according to the present invention include strong inorganic acids such as hydrochloric, sulfuric, sulfamic, phosphoric and nitric acid.

The term "disproportionation agent" or "aldehyde agent" is used to describe a number of disproportionation agents which enhance the rate of disproportionation of chlorous acid to significantly increase the amount of chlorine dioxide which is produced and minimize residual chlorite ion. The disproportion agents according to the present invention are chosen for their ability to substantially enhance the rate and efficiency (yield) at which chlorine dioxide is formed from chlorous acid (even at relatively high pH's and low concentrations of acid—a consideration in the embodiments which minimize corrosion) when an acid and a salt of chlorite are combined in aqueous solution, for their ability to form their biologically compatible substantially non-toxic organic acid side products and for their ability to minimize residual chlorite ion. Thus, by using a disproportionation agent according to the present invention, one can produce effective quantities of chlorine dioxide, minimize the amount of acid used and raise the pH of the chlorine dioxide-generating solution to a non-corrosive level, if desired.

Disproportionation agents for use in the present invention preferably include hydroxyl free aldehydes, most preferably, substantially non-toxic hydroxyl free aldehydes such as acetaldehyde, benzaldehyde, glutaraldehyde, cinnamic aldehyde, propionaldehyde, paraldehyde, 2-Furfural (bran oil) and 5-Hydroxymethyl-2-furfural (5HMF), among others. Preferred disproportionation agents for use in the present invention include those aldehydes that are substantially non-toxic themselves and which are converted during the disproprotionation process to substantially non-toxic side products. The hydroxyl free aldehydes acetaldehyde, benzaldehyde, glutaraldehyde and propionaldehyde are particularly preferred for use in the present invention. Hydroxyl free aldehyde compounds are preferred over hydroxyl containing aldehyde compounds for use in the present invention, because of the tendency of the hydroxyl containing aldehydes to undergo an aldol condensation in solutions at low pH.

The term "pharmaceutically acceptable salt" or "salt" is used throughout the specification to describe a salt form of one or more of the compositions herein which are presented to increase the solubility of the compound in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. The term "salt" shall mean any salt consistent with the use of the compounds according to the present invention.

The term "in conjunction with" shall mean that at least one additional anticancer agent is used in conjunction with, but not at the same time as, the chlorine dioxide composition. The additional anticancer agent is often administered to the patient at different times in order to avoid complications given the broad reactivity of chlorine dioxide. Although chlorine dioxide compositions according to the present invention may be co-administered with certain additional anticancer agent to a patient at the same time, the term embraces the administration or at different times. In certain instances, chlorine dioxide compounds according to the present invention may be administered with one or more additional anti-cancer agents or other agents which are used to treat or ameliorate the symptoms of cancer, especially prostate cancer, including metastatic prostate cancer. In certain preferred aspects and in many instances, the chlorine dioxide compositions are administered in the absence of an additional anticancer agent.

The term "anticancer agent" or "additional anticancer agent" refers to a compound other than the chimeric compounds according to the present invention which may be used in combination with a compound according to the present invention for the treatment of cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6,Azgly 10] (pyro-Glu-His-Trp-Ser-Tyr-D-Ser(But)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

In addition to anticancer agents, a number of other agents may be coadministered with chimeric compounds according to the present invention in the treatment of cancer. These include active agents, minerals, vitamins and nutritional supplements which have shown some efficacy in inhibiting cancer tissue or its growth or are otherwise useful in the treatment of cancer. For example, one or more of dietary selenium, vitamin E, lycopene, soy foods, curcumin (turmeric), vitamin D, green tea, omega-3 fatty acids and phytoestrogens, including beta-sitosterol, may be utilized in combination with the present compounds to treat cancer.

The terms "radiotherapy" and "radiation therapy" are used interchangeably and describe therapy for cancer, especially including prostate cancer, which may be used in conjunction with the present compositions. Radiation therapy uses high doses of radiation, such as X-rays, to destroy cancer cells. The radiation damages the genetic material of the cells so that they cannot grow. Although radiation damages normal cells as well as cancer cells, the normal cells can repair themselves and function, while the cancer cells cannot.

Radiation therapy may be used in combination with the presently claimed compositions. Radiation therapy is most effective in treating cancers that have not spread (metastasized). But it also may be used if the cancer has spread to nearby tissue. Radiation is sometimes used after surgery to destroy any remaining cancer cells and to relieve pain from metastatic cancer.

Radiation is delivered in one of two ways: External-beam radiation therapy and branchytherapy. External-beam radiation therapy uses a large machine to aim a beam of radiation at the tumor. After the area of cancer is identified, an ink tattoo no bigger than a pencil tip is placed on the skin of the subject so that the radiation beam can be aimed at the same spot for each treatment. This helps focus the beam on the cancer to protect nearby healthy tissue from the radiation. External radiation treatments usually are done 5 days a week for 4 to 8 weeks or more. If cancer has spread, shorter periods of treatment may be given to specific areas to relieve pain.

There are basically three types of external radiation therapy: conformal radiotherapy (3D-CRT), intensity-modulation radiation therapy (IMRT) and proton therapy. Conformal radiotherapy uses a three-dimensional planning system to target a strong dose of radiation to the cancer. This helps to protect healthy tissue from radiation. Intensity-modulated radiation therapy uses a carefully adjusted amount of radiation. This protects healthy tissues more than conformal radiotherapy does. Proton therapy uses a different type of energy (protons) than X-rays. This approach allows a higher amount of specifically directed radiation, which protects nearby healthy tissues the most. Sometimes proton therapy is combined with X-ray therapy.

Radiation therapy may combine brachytherapy with low-dose external radiation. In other cases, treatment combines surgery with external radiation. In the present invention, compounds which are otherwise claimed may be used as radiation sensitizers to enhance or potentiate the effect of radiation by inhibiting the ability of the cancer tissue to repair the damage done by the radiation therapy.

Formulations of the invention are used in parenteral dosage forms for injection into the cancer to be treated. Parenteral formulations may include a pharmaceutically acceptable diluent, carrier, solubilizer, emulsifier or preservative and/or adjuvant, but in many instances the compositions do not include additional components. Acceptable formulations are preferably nontoxic to recipients at the dosages and concentrations employed.

Formulations may be formulated as a gel for sustained activity and residence in the tumor to be treated using a pharmaceutically acceptable gelling agent, especially including glycerin at weight ranging from about 0.01% to about 50% by weight, often about 1% to about 10% as otherwise disclosed herein.

The pharmaceutical formulations of the invention are generally delivered parenterally by injection directly into the cancerous tumor to be treated. When parenteral administration is contemplated, the therapeutic formulations for use in this invention may be in the form of a pyrogen-free, parenterally acceptable aqueous solution.

Interestingly, the tumor injections of the present invention will remove tumors without the help of an immune system operating. Experiments proved this by applying the present invention into athymic mice where tumors are destroyed in one day and did not reappear. No toxicity was noticed in mice when the present invention was injected in the usual concentrations. In addition, the present method reduces the likelihood of metastases. and treats metastases without injecting the formulation into the metastatic cancer.

If similarly treating a normal immunocompetent animal, one would expect that the tumor removal would work equally well or better. The large mass and dispersion of an entire tumor by intense Intume oxidation will probably stimulate strong immune response, and among other possibilities, remove neoplastic remnants after the injection process. Tissue disintegration by injection of the composition of the present invention appears similar to that produced by sonication where particles and cells are finely separated or destroyed. The entire tumor and some of the surrounding tissue are completely absorbed into the wound, and many kinds of cancer associated antigens are exposed from both inside as well as outside the cancer cell. Processed debris will eventually enter the lymph and blood circulation with a good chance to become a vaccine for that particular neoplasm. Perfecting the methods of the present invention may also reduce or avoid metastases and recurrence.

Interleukin 12 (IL-12) cytokine as a cancer adjuvant can be injected into the tumor area the day after the Intume injection. This cytokine has been shown to stimulate both innate and adaptive immunity, and although not expected to remove a primary tumor by its own action, will add to existing cancer suppression, especially angiogenesis. The well known uncomfortable side effects of IL-12 are avoided by direct injection into the tumor rather than utilized I.P., I.V. or S.C.

The present invention can support other cancer therapies, and the length of treatment time or chemical additives applied by ensuing therapy can now be reduced. Established tumors have many mechanisms for suppressing an antitumor response, including T cell malfunction and disruption of antigen presentation. But the chief cancer mechanism, widely being studied at present, establishes "immune checkpoints" that stop the body's natural immunity pathway to the tumor. Many new inhibitors of these critical check points are antibodies which have been developed or are in the pipeline. Over the past ten years, research costs and the practical application of removing immune "checks" has run into the billions of dollars. The FDA has approved three check point inhibitors, and another dozen are under development. The global market for oncology drugs is now approaching $100 billion a year (according to IMS Health, a medical data company).

Some inhibitor antibodies have made a dramatic improvement in overall survival of patients with advanced melanoma and lung cancer. Much is expected in the near future of this new approach to oncology. However, scientific development has not been particularly successful treating a large percent of these patients. One recent phase 111 melanoma trial resulted in only a 32% overall response rate, and in another recent trial, 20% of the patients had a survival of only 3 years.

The application of breakpoint antibodies brings with it a variety of unique adverse side effects which appear as unpleasant or dangerous as with standard chemo or radio therapy. Unfortunately, too, there is often a long delay before regression or other encouraging results are seen after the initiation of break antibody. Time lag could be 6 months or more during which natural immunotherapy is not operating. Removing the primary tumor or tumors producing or "co-opting the check" would greatly shorten the delay.

The chlorine dioxide solution and gel, especially including the storage stable chlorine dioxide complex according to the present invention are generally considered non inflammatory. The medication is an excellent antiseptic for healing animal wounds and diseases, and as used experimentally on people. Injection therapy into human tumors may be simpler than surgical resection.

EXAMPLES

One application which has never been mentioned or hinted about was the injection of ClO2 into tumors. Once in a tumor the compound will oxidize polyamines found in great number in all tumors. When polyamines are oxidized, acrolein and H2O2 are formed in the tumor. Both of these are poisonous to tissue and can destroy the tumor although ClO2 itself is not toxic. The use of ClO2 in the standard way, mixing and acid with chlorite to release the gas, may be used in the present invention, but is not practical in a hospital operating room setting. In order to utilize ClO2 for universal application and in particular, in the operating room, the inventor has developed a method of stabilizing the gas in a stable single solution or gel. The solution remains stable in a wide range of pH for example 2 to 10, and will remain stable with rising temperature to about 100° F. While the usual ClO02 gas will evaporate off at temperatures well below the 100 degrees. The solution will remain stable with changing pHs and will stay stable when made at different concentrations. Adding water to the new complex solution will dilute the concentration as expected unlike diluting the ClO2 made from Acid/chlorite formation which affects the starting ingredients The new stable solution can be made at any concentration and brought to any pH after manufacture.

This stable complex when used in cancer or applied to tumors is called Intume. It is manufactured into a stable complex by the addition of urea, and mixing, and lowering the pH at a particular time (after the components are all thoroughly mixed in the aqueous solution). For tumor experiments, once stabilized into the complex, the pH can be adjusted and a syringe filled, and the contents' concentration will not vary in time. The solution can be diluted as necessary by the operator at the site of therapy. Intume ClO2 can be handled easily in the operating room or laboratory since the solution is non toxic, nonodorous, and a good antiseptic which does not have to be sterilized as are most liquids and instruments in the operating room.

Example 1 Storage Stable Chlorine Dioxide Composition

For practical purposes the storage stable composition of the present invention (Intume) is usually made in batches of 5 gallons. From this concentrate different smaller samples are diluted for particular purposes and applications. For example Frontier's Earigant is diluted 6 times, and animal cage disinfection, 20 times. Ringworm on cats is difficult application and the medication is full strength. Infections in the eye are diluted 20 times and the pH brought to 7. The pH for wounds is 4.5, and dilution for diabetic ulcers is 2 times. Warts and fungus of the nail are full strength. With this kind of dilution, pH, and concentration change is less tedious with the concentrated composition than starting with different amounts of ingredients for each application and then mixing.

The 5 gallon vessel is ideally made with 6% chlorite (by weight), preferably sodium chlorite, although potassium chlorite may be readily used (aqueous solution) and 20% urea (by weight) (aqueous solution), as the active ingredients. The chlorite is first added to water and mixed for approximately 15 minutes to an hour, often ½ hour to place the chlorite completely in solution. A urea solution is then added to this and mixed for ½ hour (note that the urea can be added as a solid or concentrated liquid to the chlorite to obtain the same or similar results). Phosphoric acid is then added bringing the pH down to 2.5. This mixture is then mixed at low speed for 1 hour, then high speed for 4 hours. This method produced the least amount of fumes and the highest complex concentration at pH 3. In about a day and ½ the solution completely clears and there is no chlorine dioxide odor. We now have a stable chlorine dioxide complex. If the pH is brought down to 2.5 rather than 3 the final complex oxidation power is greater. If brought down to 4, the oxidation power is less. It would appear that more ClO2 is formed in the complex at the lower pH. If the pH is not lowered at all, the complex will be weak and the time necessary for the complex to form may be a week.

So far, all research has been performed on athymic mice. Tumors were removed in one day and often didn't return, even with no immune system operating. Further research has to be performed to find the optimal complex concentrations necessary for different tumor types, and the ideal amount of solution for different tumor sizes In vitro, oxidation of odors, killing of bacteria, and the action on infections both appear to be similar between the chlorine dioxide complex and the standard two part method of releasing ClO2. Both are non-toxic and non irritating, and both are excellent for healing deep wounds and ear infections. Since the complex is no longer a gas, the gel or solution of ClO2 is more stable.

So far, the complex has been applied to human brain tumors, breast and prostate tumors growing in athymic mice. These animals do not reject the tumors. Success has come fairly quickly, in about one year's experimenting I have zeroed in on the approximate concentration of complex oxidation needed to remove the tumors and the volume of solution to destroy the tumors but not injure the surrounding tissue. For example, in a tumor about 1 and ½ inches in all three dimensions, about 250 micro liters is a good starting point with a concentration equivalent to about 200 (100 to 1000, preferably 100 to 800) ppm ClO2. The inventor found there were two good ways of injecting: place the syringe needle into one side of the tumor all the way into a little past the center at 5 injection points and slowly withdraw the needle all the way out as a small amounts of the composition is injected. This would produce 5 streaks. Southern Research operated on the mice this way and the tumors collapsed in one day. Stony Brook University placed small amounts of Intume around the inner wall of the tumor (perio), which removed the tumor in one day. In this latter case the tumor didn't return. Neutralizing the tissue around the outside of the tumor with lower concentration may have made the difference. The surrounding tissue is tainted as well apparently, and there was enough flow to neutralize the tumor center. In other embodiments, the solution is injected throughout the tumor to provide excellent results.

The next day after the Stony Book application one can see the inside of the body. The day after that healing started, and in 5 weeks all "looked new" again.

To thicken the solution to prevent leakage of the Intume solution, glycerin is one of the few additives for the purpose, nontoxic, nonoxidizable and compatible with most tissue. The amount may range from less than about 0.011% to up to about 50% by weight of the solution, often about 1% to about 10% by weight.

Treatment of Animals

The purpose of the following experiment was to evaluate the antitumor activity of intratumoral injections of specialized chlorine dioxide compounds, called Intume. Twelve mice were implanted with human prostate tumors, and all twelve tumors were completely or partially removed the day after the first injection. Concentrations of Intume and number of injections were varied in order to view this anti-tumor effect. No toxicity was noted except for one mouse that died after the second injection with undiluted Intume. Mice were euthanized when ulcers appeared or when tumors became enlarged as required by animal treatment rules. The oxidized tumors, destroyed by Intume, were potentially absorbed internally. No tumors in the intratumoral injected control mice exhibited the effect seen with Intume.

2. Materials and Methods 2.1. Animal Care

Six-week-old male athymic NCr nu/nu mice were purchased from Charles River Laboratories (Frederick, Md.) and acclimated in the laboratories for 10 days prior to experimentation (estimated date of birth: Aug. 15, 2014; date of arrival: Sep. 30, 2014). The animals were housed in microisolator cages, up to five per cage, in a 12-hour light/dark cycle. The animals received filtered Birmingham municipal water and sterilized Teklad Global 16% protein rodent diet (2016S, Harlan Laboratories, Inc.) ad libitum. No consumable enrichment was provided. Enrich-n'Nest paper rolls (the Andersons Lab Bedding Products, Maumee, Ohio) were provided in each cage. Cages were changed twice weekly. The animals were observed daily and clinical signs were noted. All experimental procedures were approved by the Institutional Animal Care and Use Committee of Southern Research. Animal laboratories of Southern Research are AAALAC accredited.

2.2. Tumor Model

A total of 21 mice were implanted with fragments of the human PC-3 prostate tumor from an in vivo passage. Each mouse was implanted SC near the right flank with a 30-40 mg tumor fragment using a 13-gauge trocar needle. The day of tumor fragments implantation was designated as Day 0. Individual tumors of 12 animals grew to 392-500 mg in weight (392-500 mm$^3$ in size) on Day 18 after tumor fragments implantation, the day of treatment initiation for experiment FPI-1. The animals were assigned to groups such that the median tumor weights in all four groups on Day 18 were as close to each other as possible (median tumor weights were 445 to 447 mg, mean tumor weights were 430 to 447 mg). Of the remaining nine mice, six mice with tumors of 512-1,089 mg were assigned to experiment FPI-1A on Day 20 after tumor fragments implantation, the day of treatment initiation.

2.3. Drug Storage

A vial with Intume was received at ambient temperature and was stored at covered with a large scab beginning on Day 21; the animal was euthanized on Day 32 due to the ulcerated tumor with an open wound.

Experiment FPI-1A.

Administration of Intume at a dose of 0.5 mg/kg/injection on a Q2Dx1 schedule (Group 1, Day 20) was tolerated in both animals injected. One animal was euthanized 7 days after injection with a tumor partially removed/absorbed) that had an ulcer that remained an open wound due to the Intume treatment which did not reach the evaluation point. The surviving animal experienced an initial weight gain followed by progressive body weight loss with a mean maximum body weight loss of 28% (8.7 g, Day 70) until the animal died on Day 72. The tumor of the surviving animal reached one tumor mass doubling in 25.3 days, which was 18.3 days longer than any control tumor. The tumor had been partially removed/absorbed due to Intume treatment the tumor area was covered with a large scab beginning four days after treatment (Day 24).

Administration of Intume at a dose of 0.5 mg/kg/injection on a Q2Dx2 schedule (Group 2, Days 20 and 22) was tolerated in both animals injected. One animal was euthanized 7 days after treatment (did not reach the evaluation point) and the other animal was euthanized 11 days after the first treatment (Day 31) with tumor removed/absorbed that had ulcers that remained an open wound due to the Intume treatment. The animal euthanized on Day 31 had a mean maximum body weight loss of 9% (2.2 g, Day 31). The tumor of the animal euthanized on Day 31 reached one tumor mass doubling in 8.1 days, which was only 1.1 days longer than any control tumor from FPI-1. Both tumors had been removed/absorbed due to Intume treatment the tumor area was covered with a large scab beginning four days after treatment (Day 24).

Administration of Intume at a dose of 0.5 mg/kg/injection on a Q2Dx3 schedule (Group 3, Days 20, 22, and 24) was tolerated in both animals injected. One animal was euthanized 11 days after treatment (Day 31) with a tumor removed/absorbed that had an ulcer that remained an open wound due to the Intume treatment which did not reach the evaluation point. The other animal was euthanized 14 days after the first treatment (Day 34) with a prolapsed penis. The animals had a mean maximum body weight loss of 10% (2.8 g, Day 31 before any animal was removed from the study). The tumor of the animal euthanized on Day 34 reached one tumor mass doubling in 12.1 days, which was 5.1 days longer than any control tumor from FPI-1. The tumor had been removed/absorbed due to Intume treatment the tumor area was covered with a large scab beginning four days after treatment (Day 24).

CONCLUSIONS

Experiment FPI-1.
  Intume was well tolerated in S out of 6 animals with one death observed 2 days after injection.
  Intume injection caused the removal/absorption of all 6 tumors in one day.
  No tumors in the control exhibited the same response.
Experiment FPI-1A.
  Intume was well tolerated in all six animals.
  Injection of diluted Intume caused the removal/absorption of all 6 tumors, which was less pronounced than the undiluted Intume suggesting a dose response.
  The tumors grew in all 6 animals after Intume injection and reached the evaluation point from 8.1 days to 25.3 days (less than any control tumor).
Further Example Cancer Treatment in Athymic Mice Experiments were conducted at Stony Brook's Division of Animal Resources (DLAR). Chlorine Dioxide Tumor Treatment solution (Example 1 composition) was provided by Frontier Pharmaceutical Inc., Melville, N.Y. In these studies, we injected tumor bearing mice to show that the chlorine dioxide solution of example dissolved tumors easily. Tumors treated were brain, breast and prostate implanted in the flanks of athymic mice using direct injections into the tumor. Initially, injections were made in the center of the tumor and this resulted in portions of the tumor still remaining, leaving ridges and overhanging tumor tissue. In these mice, it was necessary to inject the remaining tumor tissue 3 times or more for complete removal of larger sized tumors.

A variety of different formulations and injection techniques were tried. It became apparent that the concentration of the active ingredient, as well as dose volume made a difference in the treatment outcome, as did how the injection into the tumor was made.

In the last series of experiments, tumors were removed and didn't recur after a single treatment. This was done by injecting the tumor in multiple sites around the tumor edges. This appeared to be quite an accomplishment considering the mice had no immune system to help remove the tumor.

The investigators had not seen or heard about this sort of response before. These experiment should be repeated with many more mice, and larger animals also, to cement the present interesting findings.

Figure 19:
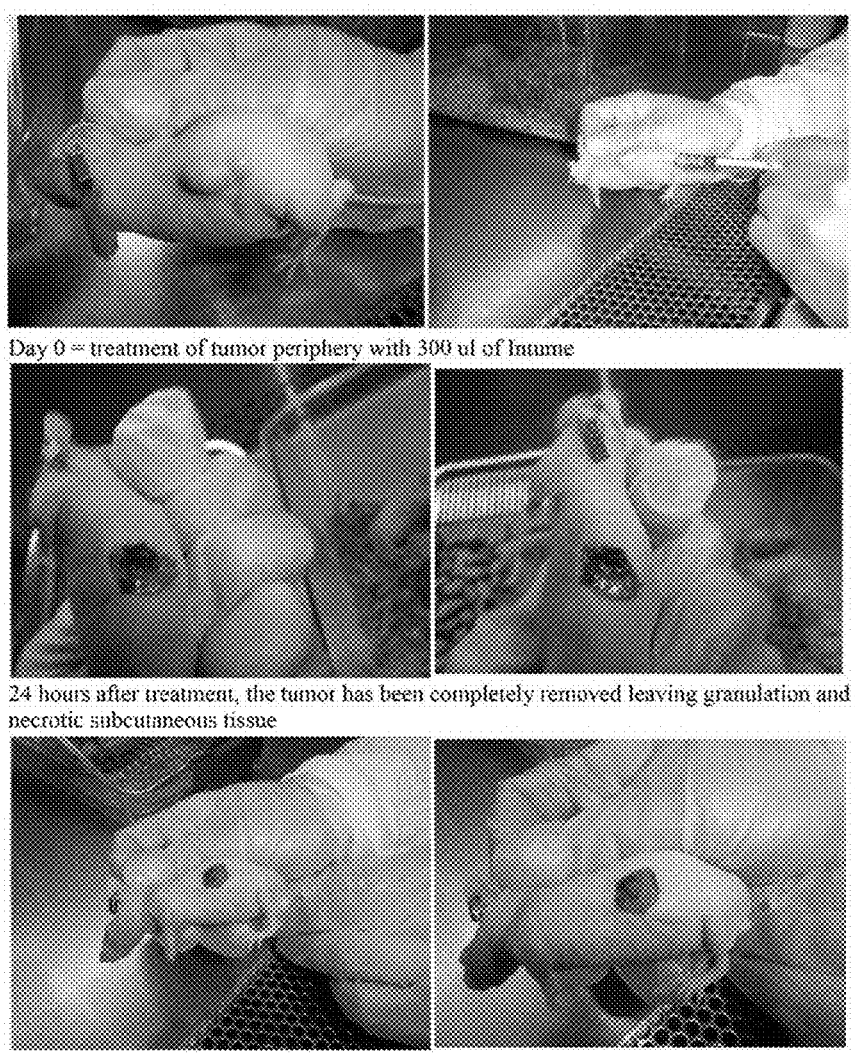
Figure 20:
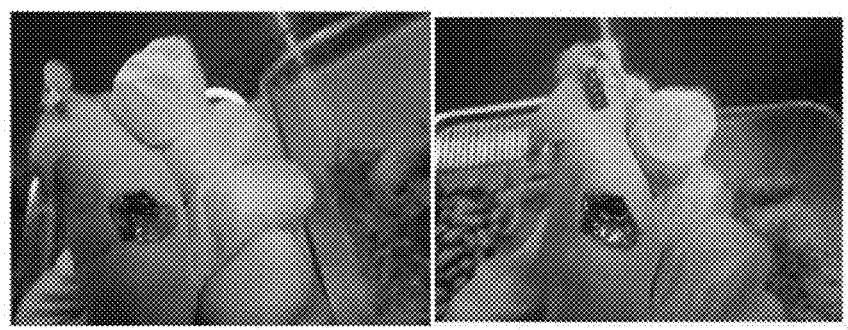
Figure 20:
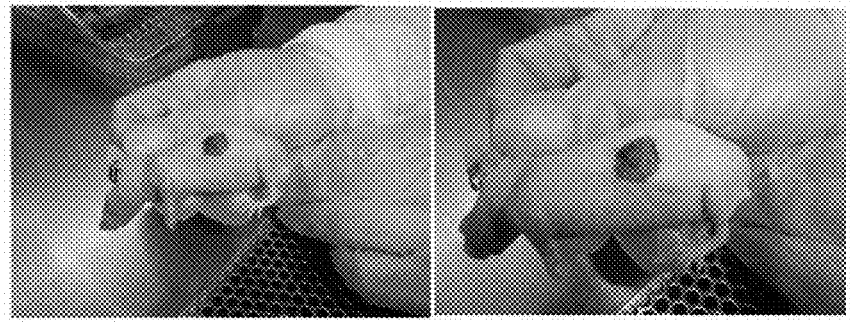
Figure 20:
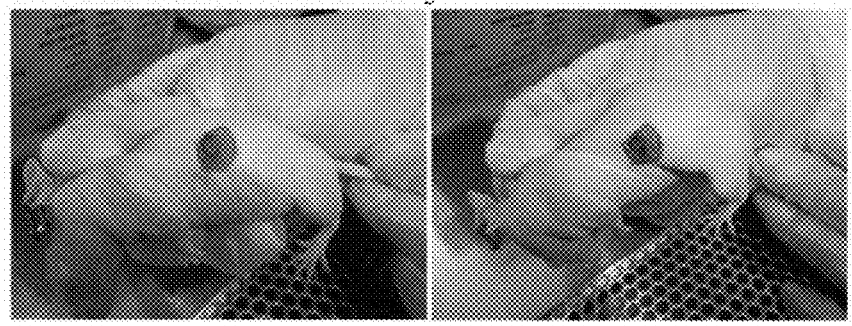

FIGS. 19 and 20 show the complete removal of the tumor in 24 hours using 300 ul of Intume™, the composition of example 1.

Toxicity Experiments
Toxicity of Chlorine Dioxide Complex on Healthy Organs in Mice
Introduction:
  A major university has been experimenting with Intume Tumor Treatment on laboratory animals for two years.

Toxicity is only noticed in injected mice if concentrations and volumes of the present composition are higher than 2 or 3 times that needed for effective tumor removal. The purpose of this study is to evaluate the toxicity of the present composition when injected directly into healthy mouse organs.

Procedure:

Part 1—Five Healthy Mice (SK1PYMT 4913×SK1FVB) were anesthetized with isothiamine, shaved and surgically opened to expose the organ to be injected with test product. The test product evaluated was Intume™ Tumor Treatment (Lot #: 3489) Supplied by Frontier Pharmaceutical, Inc. Intume was injected directly into one organ (liver, spleen, or kidney) at 50 ul doses at 25%, 50% or 100% concentration. Mice remained under anesthesia after the injection and were monitored over a 30 minute period to observe for gross signs of toxicity.

Part 2—Upon completion of Part 1, Methylene blue (MB) was injected into the same mice that were injected with INtume in Part 1. The purpose was to see how and where the test product spread throughout the body. Mice were euthanized so that internal cavity could be examined. Organs were cut in half for inspection of the extent of saturation.

Results: See Tables 1 and 2, FIGS. 21 and 22.

CONCLUSION

Part 1

Intume was injected into healthy organs at 25%, 50% and 100% concentrations. The mice were evaluated over 30 minutes. No toxicity was observed in the mice or the individual organs at any concentration.

Part 2

Injection of methylene blue dye revealed that different organs absorb and distribute dye differently from one another. The entire kidney got saturated and the dye got into the urine but did not spread throughout the body. The entire spleen got saturated with dye but none of the other organs did. The dye did not spread past the injection site in the liver.

Overall Discussion

INtume tumor injections will remove tumors completely, and without help of an immune system operating. Experiments proved this by injecting Intume Cancer Solution into athymic mice; tumors are destroyed in one day and do not recur. The mechanism of action utilizes the strong oxidation by chlorine dioxide—an aqueous non toxic antiseptic, for many years used as a treatment on animal wounds and anecdotally on humans. If injecting animals containing an intact immune system, one would expect tumor removal by similar injection would work equally well or better. Dispersing a large tumor mass by intense oxidation will produce many foreign compounds likely stimulating an immune response. (Ton N Schumacher, "Neoantigens in Cancer immunotherapy," SCIENCE, 3 Apr. 2015).

Tissue disintegration by INtume appears similar to the action produced by sonication where particles and cells are finely separated or destroyed by cavitation. The entire tumor and some of the surrounding tissue are absorbed into the wound along with the cell wall. T cells and B cells come into close association with antigens in the mix. The process may then stimulate immunogenic cell death which would train immune cells to the altered cells or neoantigens. (Lucillia Bezu, "Combinatorial strategies for the induction of immunogenic cell death," Front. immunol, 24 Apr. 2015). Immune cells with this memory may circulate through the body and destroy tumors at other sites. Alternatively, tumor debris eventually entering the lymph and blood circulation, including antigens, dendritic cells and T cells, may set the stage as a vaccine for that particular neoplasm.

As is well known, a tumor establishes immunosuppressive mechanisms, no doubt a difficulty in creating a working vaccine and other anticancer activities. (Adeegbe, Dennis, "Natural and Induced T Regulatory Cancer," Frontiers in Cells in Immunology, 2013). The suppressive regulatory arrangement consists of Treg and myeloid cells which are often found in high numbers in the tumor microenvironment, and if left in place inhibits immediate immune therapy but also influence new tumors to grow in the future. ("What is the relationship between tumors and immune tolerance," Quora, https:wwwps:// Oct. 31, 2014). The tainted microenvironment tissue could probably be inactivated by further injecting a lower Intume concentration into the surrounding area.

Interleukin 12 (IL-12) cytokine, a cancer adjuvant, when directly injected into the tumor area avoids serious side effects usually produced by cytokines. Both innate and adaptive immunity are theoretically stimulated, and although not expected to remove the primary tumor, IL-12 will add to existing cancer suppression (Colombo M P, "Amount of Interleukin 12 available at the tumor site is critical for tumor regression," Cancer Res., 2531-2534, 1996). Injections appear to elicit more potent antitumor responses when placed in the tumor whereabouts rather than I.P., I.V. or S.C. (Interleukin 12: "still a promising candidate for tumor immunotherapy?" Witold Lasek, Cancer Immunol Immunother, February 2014). Interleukin 12 cytokine is expected to overcome immunosuppressive mechanisms operating in the reactive microenvironment (Fransen M F, Arens R, "Local targets for immune therapy to cancer," Int J cancer, 2013; 132:1971-76).

INtume tumor removal can support existing cancer therapies. Treatment time and anticancer compounds normally applied in standard therapy can now be reduced, if not eliminated. Established tumors have many mechanisms for suppressing an antitumor response, such as T cell malfunction and disruption of antigen presentation. The chief cancer mechanism, widely studied at present, establishes "immune checkpoints" that stop the body's usual immunity pathway to the tumor. Possibly without a primary tumor or tumor site broadcasting anti immunity, check points will naturally disappear for this neoplasm, certainly a help in preventing metastasis.

Many new inhibitors (or blockade) of critical check points are antibodies commercially developed or are in the pipeline. Over the past ten years, research costs and the practical application of removing immune "checks" has run into the billions of dollars. The FDA has approved four inhibitors, and another dozen are under development. The global market for oncology drugs is now approaching $100 billion a year (according to IMS Health, a medical data company). The cost to a patient for antibody inhibitor treatment can be $150,000 per year.

Some inhibitor antibodies have made a dramatic improvement in overall survival of patients with advanced melanoma and lung cancer. Much is expected in the near future of this blockade approach to oncology. However, scientific development has not been particularly successful in a large percent of these patients. One recent phase III melanoma trial resulted in only a 32% overall response rate, and in another recent trial, 20% of the patients had a survival of 3 years.

The application of breakpoint antibodies brings with it a variety of unique adverse side effects which appear as unpleasant and dangerous as with standard chemo or radiation therapy. Checkpoint inhibitors, for example, can slow down vital organs—pituitary, adrenal, and thyroid glands. Unfortunately, too, there is often a long delay before regression or other encouraging results are seen after the initiation of antibody. Time lag could be 6 months or more during which natural immunotherapy is not operating. One could assume this time lag would be shortened with the primary tumor gone.

INtume chlorine dioxide solution or gels used in the past applied may be considered non toxic and non inflammatory in the cancer setting, unlike cytotoxicity of more common oxidants, hydrogen peroxide, bleach. ozone, or peracetic acid. Successful tumor injections will probably require a single session only, and wind up with relatively few side effects. When surgery or taxol treatment must be avoided, the option of injecting tumors may be valuable even without the promise of immunological intervention.

REFERENCES

[i] Walker H, et al. Topical use of sodium chlorite-lactic acid gel in pseudomonas burn wound sepsis. US Army Institute of Surgical Research, Fort Sam Houston Tex. 1981

[ii] Kenyon A, et al. Controlled wound repair in guinea pigs, using antimicrobials that alter fibroplasias. Am J Vet Res, Vol 47, No. 1 Jan. 1986

[iii] Kenyon K, et al. Comparison of antipseudomonad activity of chlorine dioxide/chlorous acid-containing gel with commercially available antiseptics. Am J Vet Res, Vol 47, No. 5, May 1986.

[iv] Lubbers, J, et al. Effects of the chronic oral administration of chlorine dioxide, chlorate, chlorite and chloramines to normal healthy volunteers; A controlled study. The Pharmacologist, Vol 22, No 3, 1980. P. 171

[v] Mohammad A, et al. Clinical and microbiological efficacy of chlorine dioxide in the management of chronic atrophic candidiasis: an open study. International Dental Journal (2004) 54, 154-158.

[vi] Chapnick A. Report from veterinary surgeon who performed over 100 animal surgeries. Veterinary Healthcare Associates. 3025 Dundee Rd, Winter haven, Fla. 33884.

[vii] MB Research Labs. Vaginal toxicity in rabbits. Project #MB 99-7837.22 Spinnerston, Pa. Jan. 4, 2000

[viii] US Department of Health and Human Services. Toxicological profile for chlorine dioxide and chlorite. September 2004. 141 pages

[ix] Soda K. The mechanisms by which polyamines accelerate tumor spread. Journal of Experimental and Clinical Cancer Research 2011, 30:95

[x] Luk G D, Casero R A Jr. Polyamines in normal and cancer cells. Adv Enzyme Regul. 1987; 26:91-105

[xi] Gerner E W, Meyskens F L Jr. Polyamines and cancer: old molecules, new understanding. Nature Reviews, Cancer Vol 4, October 2004, 781-792

[xii] Bachrach U. Polyamines and Carcinogenisis. Scientific Journal of the Faculty of medicine in Niš 2012; 29(4): 165-174

[xiii] Hesselink T L, et al. The science behind the treatment. On the mechanisms of toxicity of chlorine oxides against malarial parasites—an overview. Genesis II, Costa Rica. Sep. 6, 2007. Http://genesis2costarica.org/science-of-chlorine-dioxide/

[xiv] DeGruyter W. Gene therapy—induced by polyamines. ACTA Facultatis Medicae Naissensis, 2012, vol 29, No 4. pg 172

[xv] Alarcon R A. Anticancer system created by acrolein and hydroxyl radical generated in enzymatic oxidation of spermine and other biochemical reactions. Med Hypotheses. 2012 October; 79(4):522-30.

[xvi] Frei B, Lawson S. Vitamin C and cancer revisited. Proceedings of the National Academy of Sciences. Vol. 105, No. 32. Aug. 5, 2008.

[xvii] Contreras E Sr. Contreras metabolic integrative therapy research. Chapter 5: oxidizing cancer to death. Oasis of Hope Hospital Integrative Regulatory Therapy Research. http://www.oasisofhope.com/irt_ch5_oxidizing_cancer.php

[xviii] Halliwell B, et al. Hydrogen Peroxide in the Human Body. GAIA Organics. FEBS Letters, 486(1), 2000 Federation of European Biochemical Societies.

[xix] Douglas D M, et al. Mechanism of action of a potential wound-healing compound, Alcide. Presented at Second international Symposium On Tissue Repair Biological and Chemical Aspects. May 13, 1987.

[xx] Ruttimann J. Macrophages and nitric oxide: A deadly combination. The Journal of Experimental Medicine. JEM Home, 2007 Archive, 24 December, Ruttimann 204 (13): 3057

[xxi] Liou G Y, Storz P. Reactive oxygen species in cancer. Free Radic Res. 2010 May; 44(5):479-96

[xxii] Gibellini L, et, al. Interfering with ROS Metabolism in Cancer Cells: The Potential Role of Quercetin. Cancers 2010, 2(2) 1288-1311

[xxiii] DiStefano J F, et al. Role of Tumor Cell Membrane-bound Serine Proteases in Tumor-induced Target Cytolysis. Cancer Research 42, 207-218, January 1982.

[xxiv] Danish-Chinese Centre for Protease and Cancer. The National Science Foundation of China. The Danish National Research Foundation. Proteases and Cancer. www.proteaseandcancer.org

[xxv] Brinckerhoff C E, et al. Interstitial Collagenases as Markers of Tumor Progression. Clin Cancer Res Dec. 2000 6; 4823

[xxvi] Weiss S J, et al. oxidative autoactivation of latent collagenase by human neutrophils. Science. 1985 Feb. 15; 227(4688):747-9

[xxvii] Hanchen Li, et al. Tumor microenvironment: The role of the tumor stroma in cancer. Journal of Cellular Biochemisrty. Vol. 101, issue 4, pages 805-815, 1 Jul. 2007

[xxviii] Bremnes R M, et al. The role of tumor stroma in cancer progression and prognosis: emphasis on carcinoma-associated fibroblasts and non-small cell lung cancer. J Thorac Oncol. 2011 January; 6(1):209-17

[xxix] Khamis Z I, et al. Active roles of Tumor Stroma in Breast Cancer Metastasis. Int J of Breast Cancer, Vol 2012 (2012), Article ID 574025, 10 pages. http://dx.doi.org/10.1155/2012/574025

[xxx] Waldner M J, et al. Interleukin-6—A key regulator of colorectal cancer development. Int J Biol Sci 2012; 8(9): 1248-1253

[xxxi] Balendiran G K, et al. The role of glutathione in cancer. Cell Biochemistry and Function. Vol 22, issue 6, pages 343-352, November/December 2004.

[xxxii] Estrela J M, et al. Glutathione in cancer biology and therapy. Critical Reviews in Clinical Laboratory Sciences. 2006, Vol. 43, No. 2 Pages 143-181.

[xxxiii] Grob H S, Dean. Research report. Adelphi University. Nov. 26 1980.

[xxxiv] Lanham J W, Section Chief, Life Sciences. Research report. McDonnell Douglas Astronautics Company, St. Louis Division. Jan. 5, 1981

[xxxv] Cagan K. Research report. Naples Laboratories Microbiologists, Long Beach Calif. Dec. 1 1979 xxxvi Barber T L, Research Veterinary Medical Officer. Research report. US Dept of Agriculture, Science and Education Administration. Agricultural Research Western Region. Arthropod-borne Animal Diseases Research, Denver, Colo. Oct. 3, 1980.

xxxvii Scatina J, et al. Pharmacokinetics of Alcide, a Germicidal compound in rat. Journal of Applied Toxicology Vol 3, No. 3 1983. Pg 150- xxxviii Lubbers J R, et al. Controlled clinical evaluations of chlorine dioxide, chlorite and chlorate in man. Environmental Health Perspectives. Vol. 46, pp. 57-62, 1982 xxxix Abdel-Rahman, et al. Metabolism and Pharmacokinetics of alternate drinking water disinfectants. Environmental health Perspectives. Vol 46, pp. 19-23, 1982 xl Carlton B D, et al. Reproductive effects in Long Evans rats exposed to chlorine dioxide. Environ Res 1991. December; 56 (2): 170-7 xli Ohnishi K, et al. Prospective randomized controlled trial comparing percutaneous acetic acid injection and percutaneous ethanol injection for small hepatocellular carcinoma. Hepatology Vol. 27, No. 1 1998 pg:67-72 xlii Curley S A, et al. Nonsurgical therapies for localized hepatocellular carcinoma: Radiofrequency ablation, percutaneous ethanol injection, thermal ablation, and cryoablation, Wolters Kluwer Health xliii Fartoux L, et al. Treatment of small hepatocellular carcinoma with, acetic acid percutaneous injection. A single French center experience. Gastroenterologie Clinique et Biologique. Vo. 29, No 12, December 2005 xliv American Cancer Society. Questionable methods of cancer management: hydrogen peroxide and other hyperoxygenation therapies. CA Cancer J Clin. 1993; 43:47-56 xlv Schultz S, et al. Treatment with ozone/oxygen-pneumoperitoneum results in complete remission of rabbit squamous cell carcinomas. Int J Caner 2008; 122910): 2360-7 xlvi Danila M, et al. Percutaneous Ethanol Injection Therapy in the Treatment of Hepatocarcinoma—Results Obtained form a Series of 88 Cases. Dept. Gastroenterology and Hepatology, Univ. of Medicine and Pharmacy Timisoara, Romania. J Gastrointstin Liver Dis. September 2009 Vol. 18 No. 3, 317-322 xlvii Shi-Ming Lin, Percutaneous Local Ablation in Small Hepatocellular Carcinoma, Liver Research Unit, Chang Memorial Hospital, Taipei, Chang Gung Memorial Hospital, Taoyuan xlviii Piccolo S. Twist of Fate. Scientific American. October 2014, Pages 75-81 xlix Vaupel P. The Role of hypoxia-induced Factors in Tumor Progression. The Oncologist. November 2004 Vol. 9 Supplement 5 10-17 l Mahoney D J, et al. Virus Therapy for Cancer. Scientific American, November 2014. Pages 54-59.

The invention claimed is:

1. A method of treating a cancerous tumor in a patient or subject in need comprising administering an effective amount of a composition comprising a solution of chlorine dioxide stabilized with urea, thiourea or monomethylurea wherein said composition is administered directly into the tumor to be treated.

2. The method according to claim 1 wherein said stabilized chlorine dioxide solution comprises urea or thiourea.

3. The method according to claim 1 wherein said stabilized chlorine dioxide solution comprises urea.

4. The method according to claim 3 wherein said stabilized chlorine dioxide solution is prepared by combining a chlorite solution and urea in solution, mixing thoroughly to provide a mixed chlorite/urea solution and adding an acid to the chlorite urea solution, mixing thoroughly to provide a chlorite/urea/acid final solution and allowing the final solution to clarify to provide the stabilized chlorine dioxide solution.

5. The method according to claim 1 wherein said chlorine dioxide composition is an aqueous solution of chlorine dioxide.

6. The method according to claim 1 wherein said chlorine dioxide composition is a gelled solution of chlorine dioxide.

7. The method according to claim 6 wherein said gelled solution comprises glycerin in an effective amount as the gelling agent.

8. The method according to claim 1 wherein said method comprises administering said chlorine dioxide composition a single time directly into said cancerous tumor.

9. The method according to claim 8 wherein said method comprising injecting said composition directly into the core of the cancerous tumor.

10. The method according to claim 1 wherein said method comprises administering said chlorine dioxide composition in multiple sites in the cancerous tumor.

11. The method according to claim 1 wherein said method comprises administering said chlorine dioxide composition throughout said cancerous tumor.

12. The method according to claim 1 wherein said cancerous tumor is a cancer selected from the group consisting of carcinoma, lymphoma, melanoma and sarcoma.

13. The method according to claim 1 wherein said cancerous tumor is a squamous-cell carcinoma, adenocarcinoma, hepatocellular carcinoma or a renal cell carcinoma.

14. The method according to claim 1 wherein said cancerous tumor is a cancer of the bladder, bowel, breast, cervix, colon, esophagus, head, kidney, liver, lung, neck, ovary, pancreas, prostate, or stomach, Burkitt's lymphoma, Non-Hodgkin's lymphoma, melanoma, Ewing's sarcoma, hemangiosarcoma, Kaposi's sarcoma, liposarcoma, myosarcomas, peripheral neuroepithelioma, synovial sarcoma, glioma, astrocytoma, oligodendroglioma, ependymoma, gliobastoma, neuroblastoma, ganglioneuroma, ganglioglioma, medulloblastoma, a pineal cell tumor, meningioma, meningeal sarcomas, neurofibroma, Schwannoma.

15. The method according to claim 1 wherein said cancerous tumor is bowel cancer, breast cancer, prostate cancer, cervical cancer, uterine/endometrial cancer, lung cancer, ovarian cancer, testicular cancer, thyroid cancer, esophageal cancer, pancreatic cancer, stomach cancer, liver cancer, colon cancer, melanoma, Hodgkin's disease, Wilms' tumor and teratocarcinoma.

16. The method according to claim 1 wherein said treatment is combined with radiation therapy.

17. The method according to claim 1 wherein said composition is co-administered with at least one additional anticancer agent.

18. The method according to claim 17 wherein said additional anticancer agent is an antimetabolite, an inhibitor of topoisomerase I and II, an alkylating agent, a microtubule inhibitor or a mixture thereof.

19. The method according to claim 17 wherein said additional anticancer agent is everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6,Azgly 10] (pyro-Glu-His-Trp-Ser-Tyr-D-Ser(But)-Leu-Arg-Pro-Azgly-NH$_2$ acetate [$C_{59}H_{84}N_{18}Oi_4$-($C_2H_4O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenyialanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa or a mixture thereof.

20. A method of treating a cancerous tumor in a patient or subject in need comprising administering into the tumor an effective amount of a chlorine dioxide composition comprising chlorine dioxide in an amount ranging from about 5 parts per million to about 1,000 parts per million, urea in an amount ranging from about 5 parts per million to about 50,000 parts per million and an acid effective to lower the pH of the composition to less than 4.5.

21. The method according to claim 20 wherein said composition is injected directly into the core of the tumor.

22. The method according to claim 20 wherein said composition is injected into multiple sites of the tumor.

23. The method according to claim 20 wherein said composition is injected throughout said tumor.

\* \* \* \* \*